(12) United States Patent
Kappus et al.

(10) Patent No.: US 11,318,032 B2
(45) Date of Patent: May 3, 2022

(54) SPHINCTER ASSIST DEVICE AND METHOD OF USE

(71) Applicant: Covidien LP, Mansfield, MA (US)

(72) Inventors: John J. Kappus, Louisville, CO (US); Joe D. Sartor, Longmont, CO (US); John A. Hammerland, III, Arvada, CO (US); David N. Heard, Boulder, CO (US)

(73) Assignee: Covidien LP, Mansfield, MA (US)

( * ) Notice: Subject to any disclaimer, the term of this patent is extended or adjusted under 35 U.S.C. 154(b) by 119 days.

(21) Appl. No.: 16/829,028

(22) Filed: Mar. 25, 2020

(65) Prior Publication Data

US 2020/0222220 A1 Jul. 16, 2020

Related U.S. Application Data

(63) Continuation of application No. 15/595,624, filed on May 15, 2017, now Pat. No. 10,603,199.

(51) Int. Cl.
*A61F 5/00* (2006.01)
*A61B 17/00* (2006.01)
(Continued)

(52) U.S. Cl.
CPC ........ *A61F 5/005* (2013.01); *A61B 17/12009* (2013.01); *A61F 2/0004* (2013.01);
(Continued)

(58) Field of Classification Search
CPC ...... A61F 2/0004; A61F 5/0079; A61F 5/005; A61F 2/0036; A61F 2/0022;
(Continued)

(56) References Cited

U.S. PATENT DOCUMENTS 7,288,064 B2 10/2007 Boustani
7,351,198 B2 4/2008 Byrum et al.
(Continued)

FOREIGN PATENT DOCUMENTS

CN 102488571 A 6/2012
FR 2944432 A1 10/2010
(Continued)

OTHER PUBLICATIONS

Ganz, et al., "Esophageal Sphincter Device for Gastroesophageal Reflux Disease", The New England Journal of Medicine, vol. 368, No. 8, pp. 719-727 (2013).
(Continued)

*Primary Examiner* — Kaylee R Wilson
(74) *Attorney, Agent, or Firm* — Carter, DeLuca & Farrell LLP

(57) ABSTRACT

A sphincter assist device includes a plurality of interconnected and adjacent links which define a ring. Each link includes a body section and a latch cam. The body section includes a first set of side beams and a first set of snap arms. The latch cam includes a post extending from the body section and a cam disposed at an end portion of the post. The cam is engagable with the first set of snap arms of an adjacent link. Translation of the cam displaces the first set of snap arms and the first set of side beams to transition the sphincter assist device between open and closed configurations. The first set of snap arms, in combination with the first set of side beams, exert a positive non-linear force profile on the cam, thus defining a non-linear force profile of the sphincter assist device between the open and closed configurations.

18 Claims, 13 Drawing Sheets

(51) Int. Cl.
*A61F 2/00* (2006.01)
*A61B 17/12* (2006.01)
*A61F 2/04* (2013.01)
*A61B 17/132* (2006.01)

(52) U.S. Cl.
CPC .......... *A61F 2/0022* (2013.01); *A61F 2/0036* (2013.01); *A61F 5/0079* (2013.01); *A61B 17/132* (2013.01); *A61B 2017/00827* (2013.01); *A61B 2017/00876* (2013.01); *A61F 2002/044* (2013.01); *A61F 2220/0033* (2013.01); *A61F 2220/0091* (2013.01); *A61F 2230/0065* (2013.01); *A61F 2240/002* (2013.01); *A61F 2250/001* (2013.01); *A61F 2250/006* (2013.01); *A61F 2250/0051* (2013.01)

(58) Field of Classification Search
CPC ........ A61F 2220/0033; A61F 2002/044; A61F 2240/002; A61F 2250/0051; A61F 2250/006; A61F 2220/0091; A61F 2230/0065; A61F 2250/001; A61F 2002/9155; A61F 2002/91591; A61B 17/12009; A61B 17/132; A61B 2017/00827; A61B 2017/00876; A44C 5/08; A44C 5/107; A44C 5/02; A44C 5/10; A44C 5/102; A44C 5/105
See application file for complete search history.

(56) References Cited

U.S. PATENT DOCUMENTS

| | | | |
|---|---|---|---|
| 7,458,930 B2 | 12/2008 | Meretei | |
| 7,695,427 B2 | 4/2010 | Kugler et al. | |
| 8,070,670 B2 | 12/2011 | Deem et al. | |
| 8,070,671 B2 | 12/2011 | Deem et al. | |
| 8,187,164 B2 | 5/2012 | Kugler et al. | |
| 8,715,157 B2 | 5/2014 | Berg et al. | |
| 8,734,318 B2 | 5/2014 | Forsell | |
| 8,734,475 B2 | 5/2014 | Ekvall | |
| 10,603,199 B2 | 3/2020 | Kappus et al. | |
| 2005/0283235 A1 | 12/2005 | Kugler et al. | |
| 2006/0020324 A1* | 1/2006 | Schmid | A61F 2/92 623/1.16 |
| 2006/0047180 A1 | 3/2006 | Hegde et al. | |
| 2006/0276812 A1 | 12/2006 | Hill et al. | |
| 2009/0030501 A1* | 1/2009 | Morris | A61F 2/92 623/1.15 |
| 2009/0062824 A1 | 3/2009 | Berg | |
| 2009/0209995 A1 | 8/2009 | Byrum et al. | |
| 2011/0218388 A1 | 9/2011 | Ball et al. | |
| 2012/0095484 A1 | 4/2012 | Dominguez | |
| 2012/0150214 A1 | 6/2012 | Kugler et al. | |
| 2015/0105859 A1 | 4/2015 | Frigstad et al. | |

FOREIGN PATENT DOCUMENTS

| | | |
|---|---|---|
| WO | 03101352 A1 | 12/2003 |
| WO | 2009029228 A2 | 3/2009 |

OTHER PUBLICATIONS

Extended European Search Report issued in Appl. No. EP 18171989.9 dated Oct. 17, 2018 (10 pages).

* cited by examiner

SPHINCTER ASSIST DEVICE AND METHOD OF USE

CROSS-REFERENCE TO RELATED APPLICATIONS

This application is a continuation application of U.S. application Ser. No. 15/595,624, filed on May 15, 2017, the entire contents of which being incorporated by reference herein.

BACKGROUND

Technical Field

The present disclosure relates to a sphincter assist device and, more specifically, to a sphincter assist device which maintains a desired force profile during a transition of the sphincter assist device between an open configuration and a closed configurations and a corresponding transition of the sphincter.

Description of Related Art

Patients who suffer from sphincter control deficiencies, such as, for example, gastric reflux disease, fecal incontinence, etc., have sphincters which may not close fully allowing leakage. In cases regarding gastric reflux disease, gastric juice refluxing into the esophagus may injure the esophageal mucosa and underlying muscle, causing permanent damage to the sphincter which may lead to further loss of barrier function. To counter a poorly functioning sphincter patients may be prescribed pharmaceutical remedies, such as, for example, proton-pump inhibitors, or may undergo a surgical procedure to assist closure of the sphincter. Such surgical procedures may include, for example, anti-reflux surgery, such as Nissen fundoplication, or implantation of a sphincter assist device which circumscribes the sphincter, such as, for example, a rubber band or a ring of magnetically attracted elements.

However, traditional approaches typically provide linear or non-linear force profiles which are not easily tailored to a given sphincter during the radial transition between the open and closed configurations of the sphincter assist device, and the corresponding sphincter, which may lead to adverse side effects. More specifically, such force profiles may make the necessary bodily functions difficult or impossible, such as, for example, regurgitation, belching, or the passage of large objects through the sphincter passage, or may lead to dysphagia. Further, traditional implants may migrate away from the desired placement site which could result in reduced functionality.

Accordingly, the present disclosure is directed to a sphincter assist device and method of use which addresses these and other challenges of the existing technologies.

SUMMARY

Provided in accordance with the present disclosure is a sphincter assist device. The sphincter assist device includes a plurality of interconnected and adjacent links defining a ring. Each link includes a body section and a latch cam. The body section including a first set of side beams and a first set of snap arms. The latch cam includes a post extending from the body section and a cam disposed at an end portion of the post. The cam is engagable with the first set of snap arms of an adjacent link of the plurality of links, whereby translation of the cam displaces the first set of snap arms and the first set of side beams to transition the sphincter assist device between an open configuration and a closed configuration. Further, the first set of snap arms, in combination with the first set of side beams, exert a positive non-linear force profile on the cam, and thus, define a non-linear force profile during the transition of the sphincter assist device between the open and closed configurations.

In an aspect of the present disclosure, the first set of side beams and the first set of snap arms bias the ring radially inward In yet another embodiment, at least one of the links of the plurality of links further includes a male snap fit protrusion, and at least one of the links of the plurality of links further includes a female snap fit recess, where the protrusion is engageable with the recess.

In a further embodiment, the sphincter assist device further includes a protective sheath enclosing the plurality of links.

In an embodiment, the sphincter assist device further includes a first hinge coupling each respective first side beam of the first set of side beams and a respective first snap arm of the first set of snap arms. In a further embodiment, the first hinge is a living hinge.

In another embodiment, the body section of the link further includes a second set of side beams and a second set of snap arms. The cam is configured to engage the second set of snap arms of an adjacent link and displace the second set of snap arms and the second set of side beams. The second set of snap arms, in combination with the second set of side beams, exert a negative non-linear force profile on the cam.

In a further embodiment, the second set of side beams and the second set of snap arms bias the ring radially outward.

In yet a further embodiment, the body section of the link further includes a second hinge coupling each respective second side beam of the second set of side beams and a respective second snap arm of the second set of snap arms. In a further embodiment, the second hinge is a living hinge.

In accordance with another aspect of the present disclosure, a link for use in a sphincter assist device is disclosed including a body section and a latch cam. The body section includes a first set of side beams and a first set of snap arms. The latch cam includes a post extending from the body section and a cam disposed at an end portion of the post. The cam is configured to engage the first set of snap arms of a second link, whereby translation of the cam displaces the first set of snap arms and the first set of side beams to transition the link between an open configuration and a closed configuration. Further, the first set of snap arms, in combination with the first set of side beams, exert a positive non-linear force profile on the cam, thus defining a non-linear force profile during the transition of the link between the open and closed configurations.

In an embodiment, the link further includes a protective sheath configured to enclose the link.

In another embodiment, the link further includes a male snap fit protrusion or a female snap fit recess.

In yet another embodiment, the body section further includes a first hinge coupling each respective first side beam of the first set of side beams and a respective first snap arm of the first set of snap arms. In a further embodiment, the first hinge is a living hinge.

Further still, in an embodiment, the body section further includes a second set of side beams and a second set of snap arms. The cam is configured to engage the second set of snap arms of a second link, whereby translation of the cam displaces the second set of snap arms and the second set of side beams, displacement thereof exerting a negative non-linear force profile on the cam.

In a further embodiment, the body section further includes a second hinge coupling each respective second side beam of the second set of side beams and a respective second snap arm of the second set of snap arms. In a further embodiment, the second hinge is a living hinge.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1A:
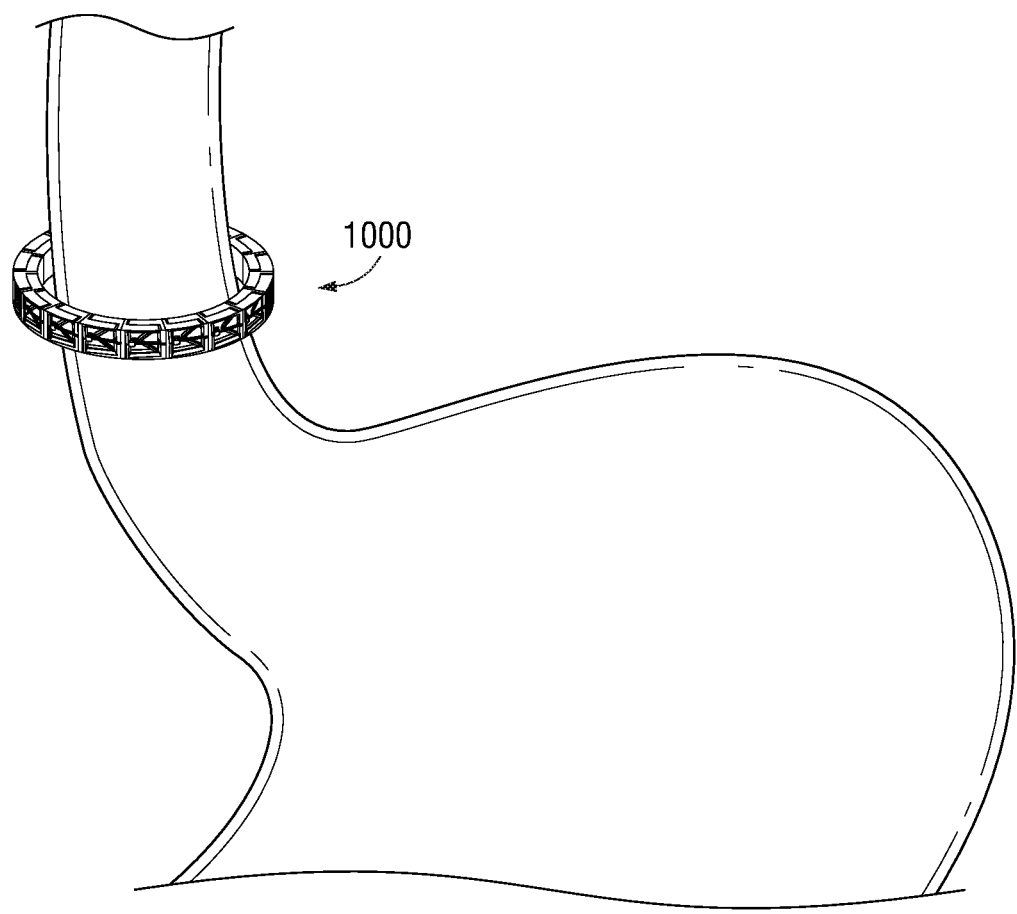
FIG. 1A is a side perspective view of an embodiment of a sphincter assist device in accordance with the present disclosure, shown in a closed configuration and positioned proximate a lower esophageal sphincter.

The present disclosure is directed to devices and methods for assisting the functionality of a sphincter. As will be discussed below, a sphincter assist device may be implanted within a patient and positioned to circumscribe the sphincter. The sphincter assist device is configured to assist the sphincter assume a tight closed position, and provide a non-linear force profile during opening and closing of the sphincter. Embodiments of the present disclosure are now described in detail with reference to the drawings in which like reference numerals designate identical or corresponding elements in each of the several views. As is understood in the art, the term "clinician" refers to a doctor, a physician, a nurse, or any other care provider or support personnel.

Figure 1B:
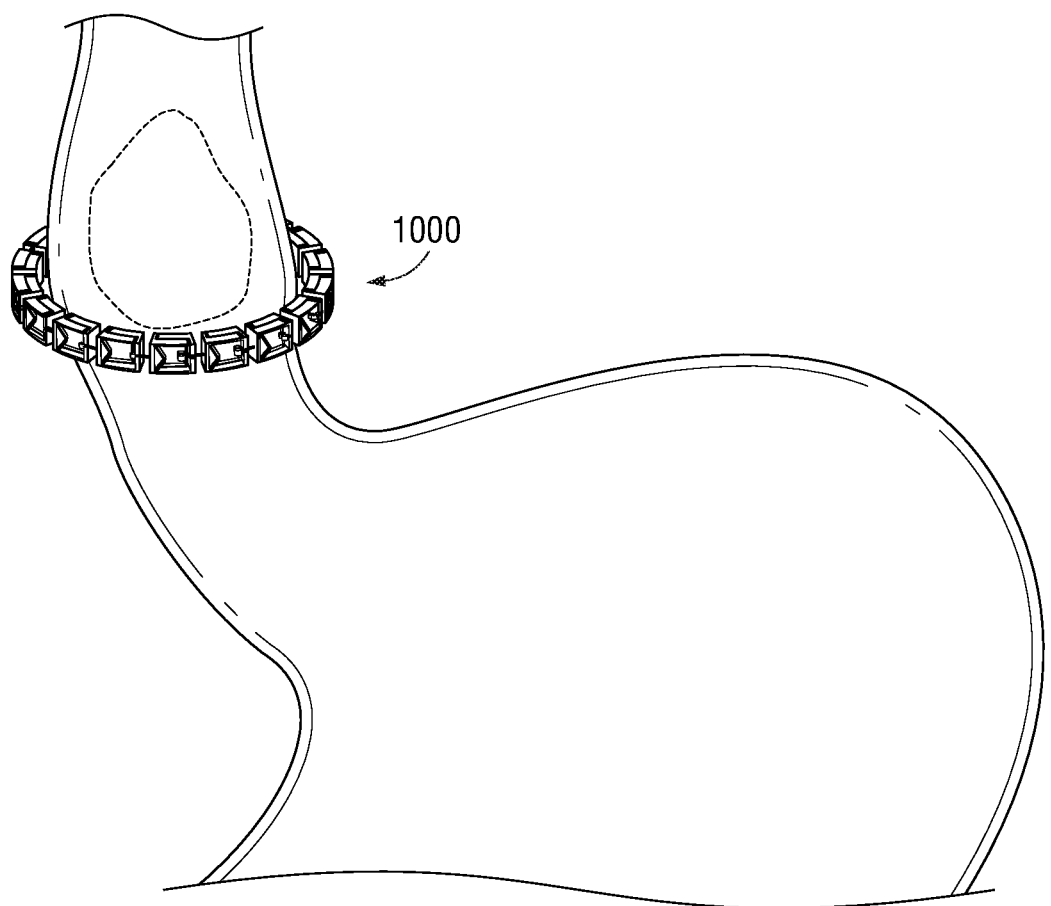
FIG. 1B is a side perspective view of the sphincter assist device of FIG. 1A shown in an open configuration.

Referring now to FIGS. 1A and 1B, an exemplary embodiment of a sphincter assist device 1000 is illustrated circumscribing a sphincter and acts as a mechanical assist device to the sphincter. It is envisioned that sphincter assist device 1000 may be utilized to assist any sphincter of a patient. For example, sphincter assist device 1000 may be implanted within a patient such that sphincter assist device 1000 circumscribes the upper or lower esophageal sphincter and provides radial compression thereof, thereby assisting the sphincter close tightly. In the example of FIGS. 1A and 1B, sphincter assist device 1000 is illustrated in use for the treatment of gastroesophageal reflux disease (hereinafter "GERD"), where sphincter assist device 1000 is placed proximate the lower esophageal sphincter and near the junction of the esophagus and the stomach.

Sphincter assist device 1000 consists of a plurality of links, as discussed below, which form a ring, and is transitionable between a closed configuration (FIG. 1A) and an open configuration (FIG. 1B). As sphincter assist device 1000 transitions between the closed and open configurations, sphincter assist device 1000 translates radially thus increasing or decreasing the inner diameter thereof. Thus, in the closed configuration sphincter assist device 1000 defines a first inner diameter which assists the sphincter maintain a tight closed position, and in the open configuration sphincter assist device 1000 defines a second, larger inner diameter such that objects may pass through the sphincter passage. It is envisioned that in the closed configuration an inner diameter of sphincter assist device 1000 may define approximately 5 mm to approximately 15 mm, whereas in the open configuration the inner diameter of sphincter assist device 1000 may define approximately 10 mm to approximately 35 mm, or any values in-between such that sphincter assist device 1000 is appropriately sized for a given sphincter of a patient. For example, sphincter assist device 1000 may define an approximate size of 5 mm to approximately 20 mm to accommodate the urethra at the bladder neck, 15 mm to approximately 25 mm to accommodate the lower esophageal sphincter, approximately 15 mm to approximately 25 mm to accommodate the pylorus sphincter, approximately 20 mm to approximately 35 mm to accommodate the rectal sphincter Additionally, or alternatively each link of sphincter assist device 1000 may be removably attached to one another, as discussed further below, such that the length of sphincter assist device 1000 may be adjusted prior to implantation. The clinician may determine and customize a length of sphincter assist device 1000 to achieve the best fit for a particular patient during or shortly in advance of a procedure.

Generally, it should be appreciated that sphincter assist device 1000 is configured to create a force profile upon the sphincter circumscribed thereby, such that the sphincter is biased radially inward in the closed position to maintain the closed position, encounters a specific resistance during the transition from the closed position towards the open position, and lastly, when in the open position encounters a minimal retracting force or reduced radially inward bias which permits the sphincter to maintain the open position while also assisting the sphincter transition back towards the closed configuration. As such, sphincter assist device 1000 is configured to define a force provide during the transition between the closed and open configurations thereof. The force profile ($F_{profile}$) of sphincter assist device 1000 is graphically represented as follows, where $F_{magnitude}$ represents the magnitude of force required to drive translation of sphincter assist device 1000, and $T_{distance}$ represents the translation distance of sphincter assist device 1000: $F_{profile}=(F_{magnitude}) \times (T_{distance})$.

Figure 2A:
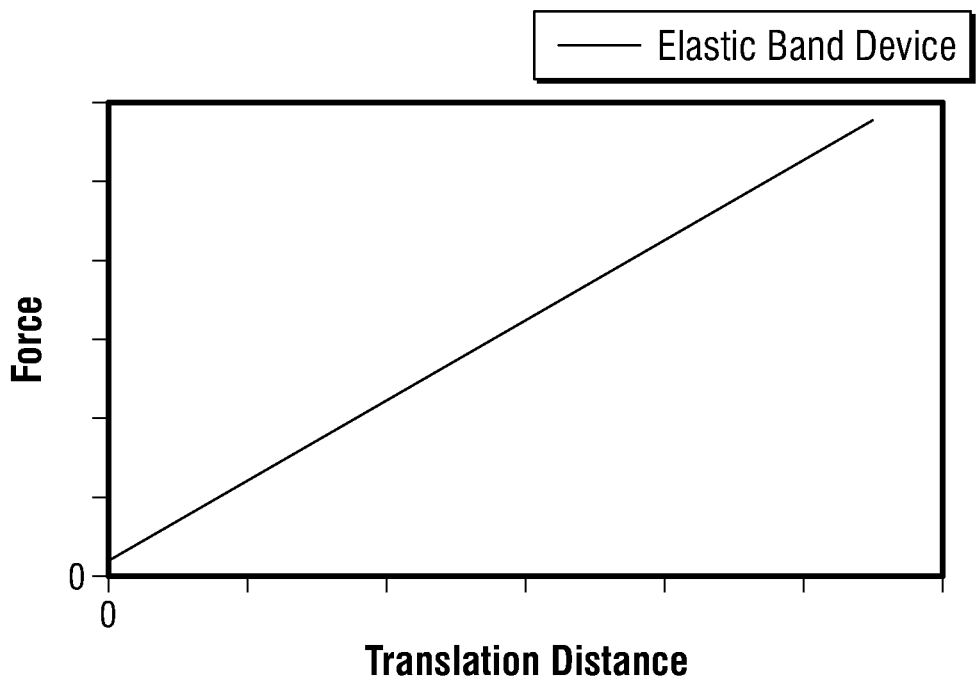
FIG. 2A illustrates an exemplary graph of force versus translation distance of a prior art elastic band device.
Figure 2B:
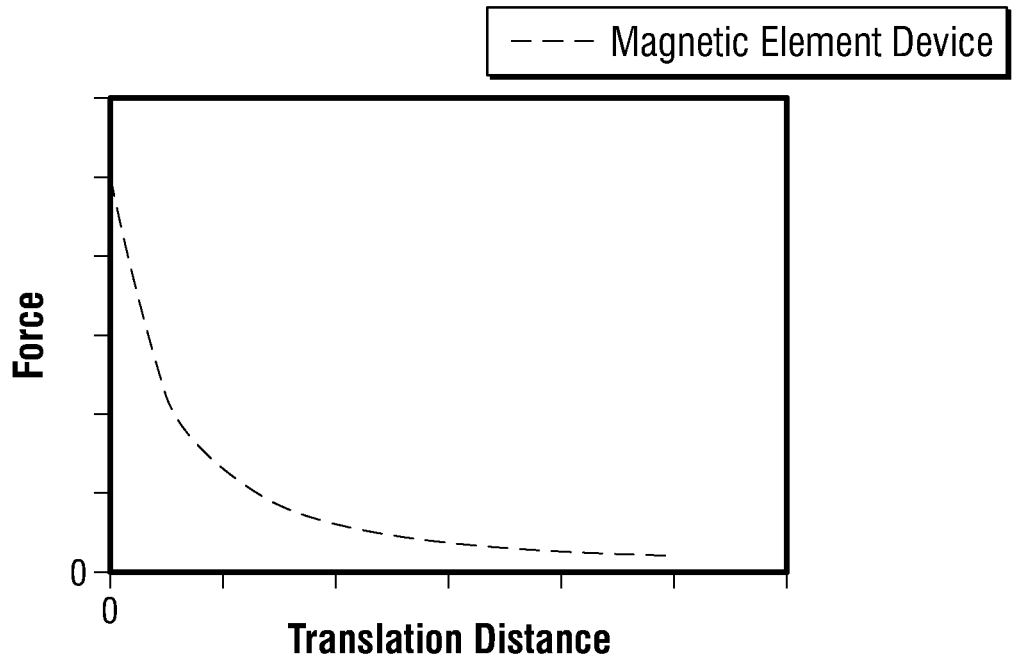
FIG. 2B illustrates an exemplary graph of force versus translation distance of a prior art magnetic element device.

Under a linear force profile, the $F_{magnitude}$ required to transition sphincter assist device 1000 from the closed configuration towards the open configuration may continue to increase, or decrease as $T_{distance}$ increases. For example, if utilizing an elastic band device $F_{magnitude}$ increases as $T_{distance}$ from the closed configuration towards the open configuration increases (FIG. 2A). Alternatively, if utilizing a device consisting of a plurality of adjacent cooperating magnetic elements, a fixed non-linear force profile is created defining a function of $(T_{distance})^2$ such that the force profile is fixed by the distance squared law of magnetic effect, whereby $F_{magnitude}$ decreases as $T_{distance}$ from the closed configuration towards the open configuration increases, and each respective magnetic element translates further away from an adjacent magnet element (FIG. 2B). In the former situation, as a result of the elastic band device the sphincter undergoes an increasing magnitude of radially inward force which reaches a maximum in the open configuration which may inhibit or prevent the passage of objects therethrough. In the latter situation, as a result of the magnetic elements, the sphincter undergoes a decreasing magnitude of radially inward force reaching a minimum in the open configuration which may inhibit or prevent the sphincter from returning to the closed position.

As discussed herein, sphincter assist device 1000 is configured to achieve a non-linear force profile during the transition between the closed and open configurations, and thus, the corresponding transition between the open and closed positions of the sphincter. A non-linear force profile provides a more gradual force requirement when transitioning sphincter assist device 1000 from the closed configuration to the open configuration, and also provides a gradual restoring force such that sphincter assist device 1000 may more easily maintain the open position, and further, may assist the sphincter return towards a tight closed position.

As the sphincter transitions from the closed configuration towards the open configuration, sphincter assist device 1000 provides the radially inward bias thereon. Thus, $F_{magnitude}$ is directed radially outward in opposition to the radially inward biasing force of sphincter assist device 1000. As $F_{magnitude}$ overcomes the radially inward bias of sphincter assist device 1000, sphincter assist device 1000 beings to transition from the closed configuration towards the open configuration. As sphincter assist device 1000 transitions from the closed configuration towards the open configuration, sphincter assist device 1000 translates radially outward and $T_{distance}$ begins to increase. As sphincter assist device 1000 approaches the open configuration, and $T_{distance}$ or $F_{magnitude}$ approaches a predetermined value, $F_{magnitude}$ decreases with respect to the $F_{magnitude}$ required to begin the transition of sphincter assist device 1000 from the closed configuration towards the open configuration. More particularly, a higher $F_{magnitude}$ is required to begin the transition of sphincter assist device 1000 from the closed configuration towards the open configuration, compared with the $F_{magnitude}$ required to maintain sphincter assist device 1000 in the open configuration. Thus, with sphincter assist device 1000 in the open configuration, the radially inward bias of sphincter assist device 1000 may more easily overcome the $F_{magnitude}$, such that sphincter assist device 1000 may transition back towards the closed configuration.

Thus, the non-linear force profile provides an initial force requirement which gradually increase as sphincter assist device 1000 initially transitions from the closed configuration towards the open configuration. After reaching an apex of required force and/or a desired translation distance, the force required to continue the transition into the open configuration, and maintain the open configuration, is reduced with respect to the amount of force initially required to begin the transition from the closed configuration to the open configuration. It should be appreciated that in the closed configuration, the non-linear force profile provides a higher magnitude of radially inward bias, with respect to the open configuration. The higher magnitude of radially inward bias thus requires a higher magnitude of force radially outward to overcome sphincter assist device 1000, such that the sphincter is assisted in maintaining a closed position. As sphincter assist device 1000 transitions towards the open configuration, the non-linear force profile provides a lower magnitude of radially inward bias, with respect to the closed configuration. The lower magnitude of radially inward bias thus requires a lower magnitude of force to overcome sphincter assist device 1000, making it easier for the sphincter to assume and maintain the open position.

Figure 3A:
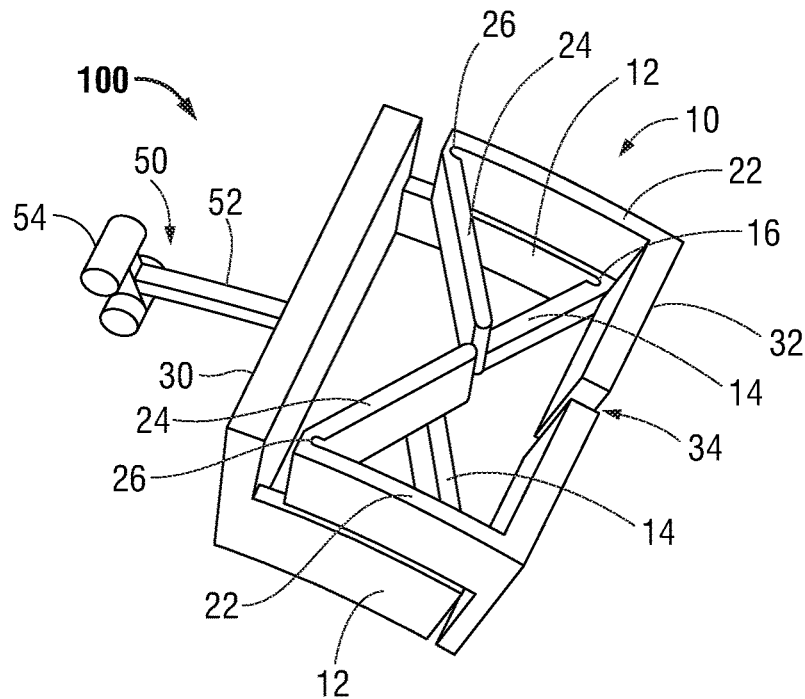
FIG. 3A is a side perspective view of an embodiment of a single link of the sphincter assist device of FIGS. 1A and 1B.
Figure 3B:
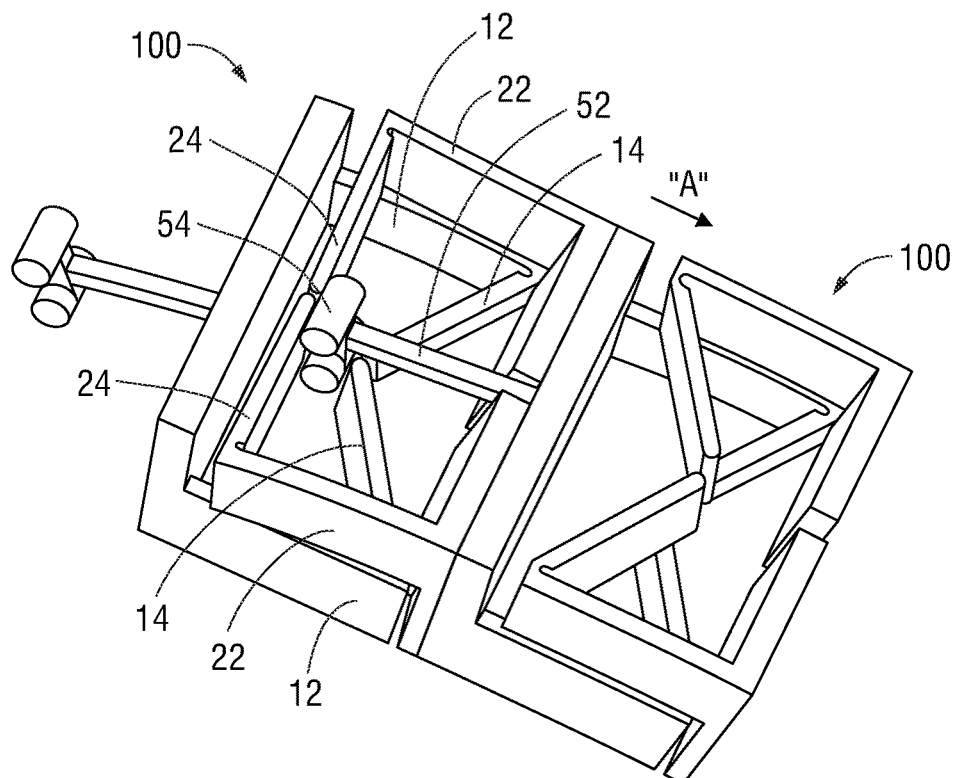
FIG. 3B is a side perspective view of a pair of links of FIG. 3A shown in the closed configuration.
Figure 3C:
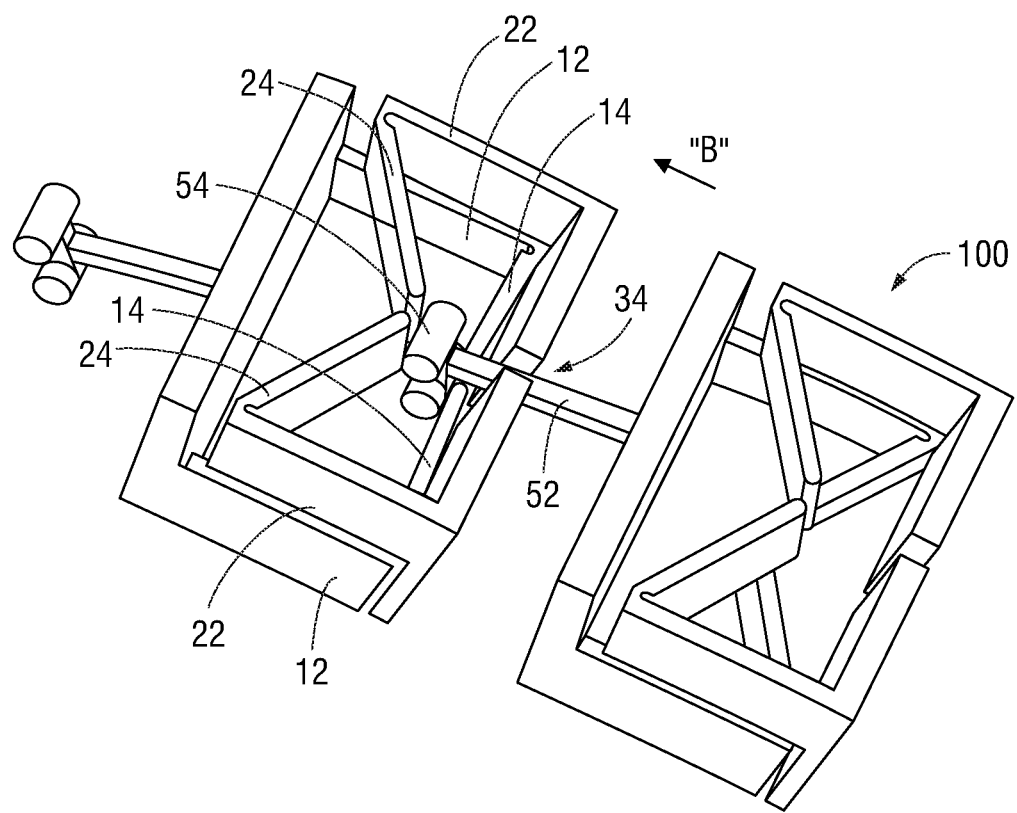
FIG. 3C is a side perspective view of a pair of links of FIG. 3A shown in the open configuration.

With reference to FIGS. 3A-3C, an embodiment of a link 100 which may make up sphincter assist device 1000 in accordance with the present disclosure is illustrated. Sphincter assist device 1000 may include a plurality of interconnected links 100, where each link 100 is sequentially coupled to an adjacent link 100 to form a ring which circumscribes the sphincter. It should be appreciated that each link 100 which makes up sphincter assist device 1000 is generally identical, unless otherwise descried herein. As described above, the non-linear force provide created by link 100 is configured such that an initial magnitude of force ($F_{magnitude}$) is required to begin the transition of sphincter assist device 1000 from the closed configuration towards the open configuration. Once the sphincter assist device 1000 achieves a desired translation distance towards the open configuration, and/or achieves a desired maximum $F_{magnitude}$, the required magnitude of force ($F_{magnitude}$) decreases and substantially drops off. Once the magnitude of force ($F_{magnitude}$) drops off, the sphincter may assume and more easily maintain the open position. Further still, link 100 provides for a similar, but opposite non-linear force profile, as discussed below. During the transition from the open configuration towards the closed configuration, the opposing non-linear force profile assists sphincter assist device 1000 transition back into the closed configuration. Thus, link 100 assists the sphincter transition from the closed position towards the open position, and also assists the sphincter transition from the open position towards the closed position.

Figure 4A:
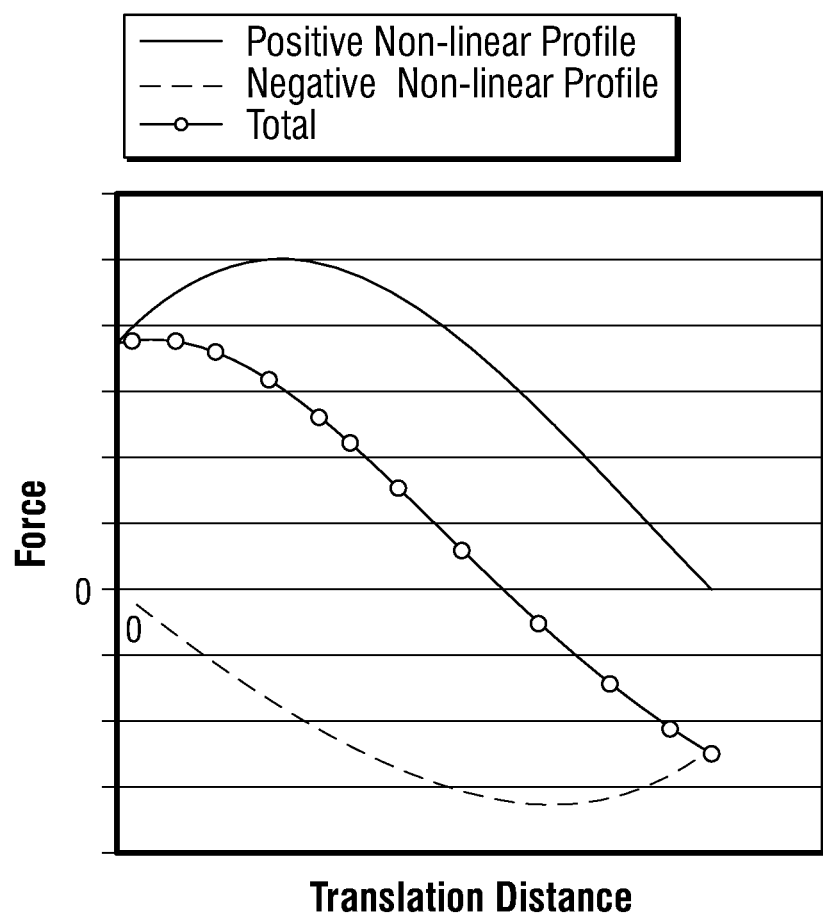
FIG. 4A is an exemplary graph of force versus translation distance of a positive non-linear force profile, a negative non-linear force profile, and a total non-linear force profile of the sphincter assist device of FIGS. 1A and 1B made up of a plurality of links of FIG. 3A.

More specifically, with link 100 making up sphincter assist device 1000, sphincter assist device 1000 is provided with both a positive spring bias and a negative spring bias. It should be appreciated that the positive spring bias created by link 100 biases sphincter assist device 1000 into the closed configuration, whereas the negative spring bias created by link 100 biases sphincter assist device 1000 into the open configuration. In such an embodiment, sphincter assist device 1000 is configured to maintain a tight closed sphincter, assist sphincter assist device 1000 transition from the closed configuration into the open configuration, and further assist sphincter assist device 1000 transition from the open configuration into the closed configuration, thus facilitating the sphincter to transition between the closed and open positions upon the passage of objects therethrough. As illustrated in the exemplary graph of FIG. 4A, which depicts ($F_{magnitude}$) versus ($T_{distance}$) from the closed configuration to the open configuration utilizing a plurality of links 100, link 100 defines a positive non-linear force profile and a negative non-linear force profile. Together, the positive and negative non-linear force profiles achieve the total non-linear force profile of sphincter assist device 1000. In this manner, the positive and negative non-linear force profiles created by link 100, and thus sphincter assist device 1000, may be individually tailored for a given sphincter of a patient.

Link 100 includes a body section 10 and a latch cam 50 extending therefrom. The body section 10 includes a first set of side beams 12 and a first set of snap arms 14 coupled thereto. A first hinge 16 is formed between each respective side beam 12 and snap arm 14. Link 100 further includes a second set of side beams 22 and a second set of snap arms 24, where second set of snap arms 24 are oriented opposite of first set of snap arms 14. A second hinge 26 is formed between each respective side beam 22 and snap arm 24. It should be appreciated that first and second hinges 16, 26 may include a living hinge to reduce components during manufacturing and assembly. The first and second hinges 16 and 26 are configured to bias the first and second sets of snap arms 14 and 24 in combination with the first and second sets of side beams 12 and 22, respectively, to assist link 100 define the non-linear force profile. The bias of the first and second hinges 16 and 26 may be tailored and configured to achieve a specific non-linear force profile for a given sphincter, as discussed further below. Latch cam 50 includes a post 52 extending from a first wall 30 of body section 10 and a cam 54 disposed near an end of post 52. Body section 10 further defines a channel 34 along a second wall 32 of body section 10 configured to receive post 52 of an adjacent link 100 therethrough.

With post 52 of a first link 100 disposed within channel 34 of a second, adjacent link 100, cam 54 engages first and second sets of snap arms 14 and 24. Post 52 is longitudinally translatable within channel 34 such that as sphincter assist device 1000 transitions from the closed configuration (FIG. 3B) to the open configuration (FIG. 3C) in the direction of arrow "A" (FIG. 3B), each respective link 100 translates away from an adjacent link 100 and post 52 longitudinally slides within channel 34. As first link 100 translates in the direction of arrow "A" away from second link 100 and towards the open configuration of sphincter assist device 1000, cam 54 pulls and displaces the first sets of snap arms 14 in the direction of arrow "A" while the second set of snap arms 24 are biased towards and move in the direction of arrow "A." As first link 100 translates in the direction of arrow "B" (FIG. 3C) towards second link 100 and the closed configuration of sphincter assist device 1000, the first set of snap arms 14 are biased towards and move in the direction of arrow "B" and cam 54 pushes and displaces the second set of snap arms 24 in the direction of arrow "B." Thus, the first and second sets of snap arms 14 and 24 transition between opposing first and second positions as cam 54 is caused to translate.

Figure 4B:
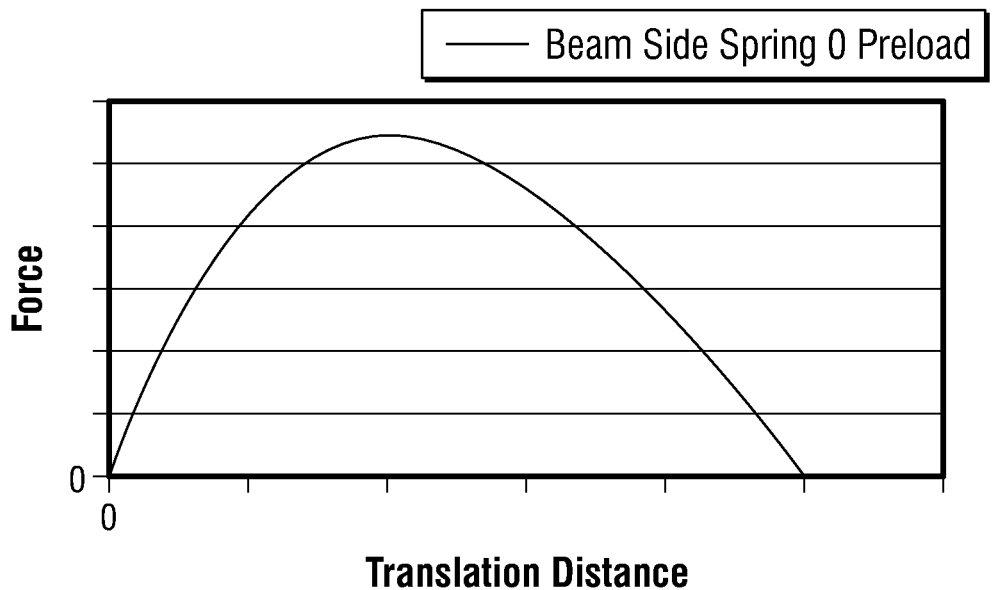
FIG. 4B is an exemplary graph of force versus translation distance of a device in accordance with the present disclosure employing the positive force arm components of the link of FIG. 3A, or the components of the link of FIG. 7A, with zero preload.
Figure 4C:
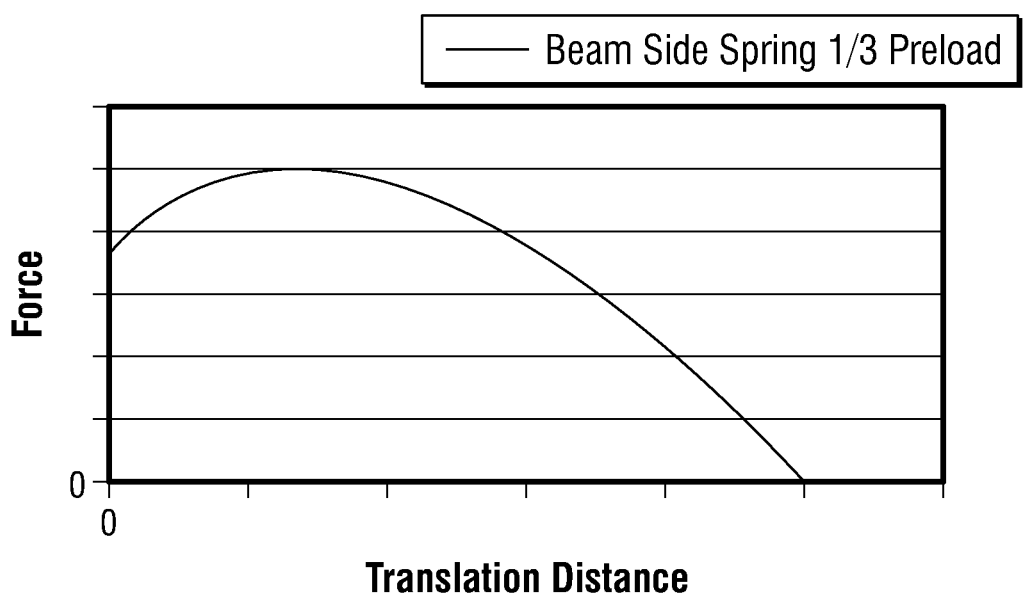
FIG. 4C is an exemplary graph of force versus translation distance of a device in accordance with the present disclosure employing the positive force arm components of the link of FIG. 3A, or the components of the link of FIG. 7A, with ⅓ preload.
Figure 4D:
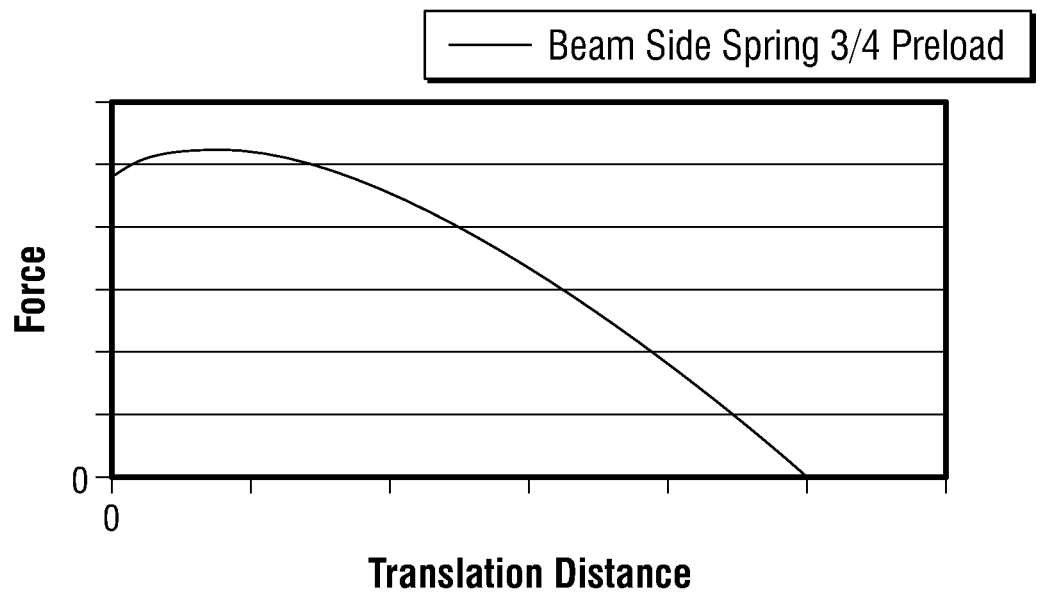
FIG. 4D is an exemplary graph of force versus translation distance of a device in accordance with the present disclosure employing the positive force arm components of the link of FIG. 3A, or the components of the link of FIG. 7A, with ¾ preload.

Each of the first and second sets of side beams 12 and 22 are flexible and act as side springs which may be preloaded with respect to body section 10. First and second sets of side beams 12 and 22 may be configured to have any spring preload value with respect to their final spring value, such as, for example, a ⅓ preloaded of the total spring value, a ¾ preload of the total spring value, or no preload. As an exemplary illustration, FIGS. 4B-4D illustrate graphs of ($F_{magnitude}$) versus ($T_{distance}$) from the closed configuration to the open configuration with varying preload values employing components of link 100 of FIG. 3A, namely, illustrating ($F_{magnitude}$) versus ($T_{distance}$) derived solely from the first set of side beams 12 and the first set of snap arms 14, being similar to that of the embodiment illustrated in FIG. 7A, as discussed below, where FIG. 4B has no preload, FIG. 4C has ⅓ preload, and FIG. 4D has ¾ preload. As illustrated, as spring preloading increases, the initial magnitude of force ($F_{magnitude}$) required to transition sphincter assist device 1000 from the closed configuration towards the open configuration increases, while the specific $T_{distance}$ wherein the magnitude of force drops off decreases. It should be appreciated that the second set of side beams 22 and second set of snap arms 24 of link 100 act similar to the first set of side beams 12 and snap arms 14, and may be configured to have the same, or differing spring preload values or directions. Together with the preload value and direction of the first set of side beams 12 and the first set of snap arms 14, the spring preload value and direction of the second set of side beams 22 and the second set of snap arms 24 contribute to the total non-linear force profile of link 100. For example, and with respect to link 100, second set of side beams 22 and second set of snap arms 24 may impart a negative force profile upon link 100, thus modifying the total non-linear force profile of link 100. Accordingly, sphincter assist device 1000 may be further tailored and configured for a given sphincter of a patient via variation of side beam preloading of the first or second sets of side beams 12 or 22 and the first and second snap arms 14 and 24 associated therewith.

Each of the first and second sets of snap arms 14 and 24 act as a "snap-action" mechanism in opposing directions. As sphincter assist device 1000 transitions from the closed configuration towards the open configuration, and cam 54 displaces the first set of snap arms 14 in the direction of arrow "A" (FIG. 3B), once post 52 travels a designed distance ($T_{distance}$) the first set of snap arms 14 "snap" into a position which defines a near zero degree relation to second wall 32 of body section 10, and thus, sphincter assist device 1000 transitions into the open configuration. As sphincter assist device 1000 transitions from the open configuration towards the closed configuration, and cam 54 displaces the second set of snap arms 24 in the direction of arrow "B" (FIG. 3C), once post 52 travels a designated distance ($T_{distance}$) the second set of snap arms 24 "snap" into a position which defines a near zero degree relation with respect to first wall 30 of body section 10, and thus, sphincter assist device 1000 transitions into the closed configuration. As a result of the snap-action mechanism of the first and second sets of snap arms 14 and 24, the magnitude of force ($F_{magnitude}$) required to transition sphincter assist device 1000 between the closed and open configurations falls off, or decrease significantly upon the "snap-action" of the first and second sets of snap arms 14 and 24. In an embodiment, the first and second sets of snap arms 14 and 24 may be inhibited from moving past the zero degree position to control or prevent a change in the direction of the force magnitude resulting from a position beyond zero degrees.

The spring preload of the first set of side beams 12 in combination with the first set of snap arms 14 and the first hinge 16 cooperatively act to create the positive spring force bias and a positive non-linear force profile upon cam 54, and thus sphincter assist device 1000, towards the closed configuration. The spring preload of the second set of side beams 22 in combination with the second set of snap arms 24 and the second hinge 26 cooperatively act to create the negative spring force bias and a negative non-linear force profile upon cam 54, and thus sphincter assist device 1000, towards the open configuration. The positive and negative spring force bias act to assist the sphincter transition between the closed and open positions under a non-linear force profile which may be tailored and configured for the given sphincter.

More particularly, in the closed configuration of sphincter assist device 1000, a portion of the first set of side beams 12 are biased inward with respect to the body section 10 as a result of the spring preload thereon, the first set of snap arms 14 start at a position away from second wall 32 of body section 10, a portion of the second set of side beams 22 are biased outward with respect to body section 10 as a result of the spring preload thereon, and the second set of snap arms 24 start at a position near zero degrees with respect to first wall 30 of body portion 10. Conversely, in the open configuration of sphincter assist device 1000, a portion of the first set of side beams 12 are biased outward with respect to the body section 10 as a result of the spring preload thereon, the first set of snap arms 14 finish travel at a position near zero degrees with respect to second wall 32, a portion of the second set of side beams 22 are biased inward with respect to body section 10 as a result of the spring preload thereon, and the second set of snap arms 24 finish travel at a position away from first wall 30. The first and second sets of snap arms 14 and 24 are configured such that when positioned away from second and first walls 32 and 30 of body portion 10, respectively, an angle is defined therebetween. It is envisioned that the first and second sets of snap arms 14 and 24 and the second and first walls 32 and 30 of body portion 10, respectively, may define any angle therebetween such that the non-linear force profile may be tailored and configured to the specific sphincter, and in an embodiment, may define an angle of 30 degrees.

It should be appreciated that sphincter assist device 1000 may be tailored and configured for a given sphincter. By configuring and adjusting, the side beam spring preloading; the angle defined between the first and second sets of snap arms 14 and 24 and the first and second walls 30 and 32 of body portion 10; the bias of the first and second hinges 16 and 26; and the manufacturing method and material choice of link 100, the non-linear force profile created by sphincter assist device 1000 may be tailored to achieve a desired non-linear force profile for a specific sphincter, a specific course of treatment, etc.

In embodiments, sphincter assist device 1000 may be constructed of stamped sheet metal or injection molded links, with or without a silicone or a biocompatible elastic tube overlying the links. In embodiments requiring a reduced size scale for sphincter assist device 1000, such as, for example, to accommodate urologic related sphincters, micro-molding or additive material manufacturing may be utilized. In further embodiments, elastomeric materials may be incorporated with respect to the snap arms to achieve the desired flexion thereof, in the millimeter scale. Further still, at the sub-millimeter scale sphincter assist device 1000 may be manufactured utilizing lithographic etching. It is further envisioned that sphincter assist device 1000 may be created from any biocompatible or Mill safe materials, such as, for example, non-metals or non-ferrite stainless steel, titanium, or alloys thereof, which are compatible with biocompatible platting. In embodiments utilizing molding manufacturing, polyolefin, nylon, polycarbonate, polyether ether ketone, polyetherimide, polysulfone, or combinations thereof may be used. It should be appreciated that utilization of molding manufacturing may be achieved via injection molding, micro-molding, 3-D printing, or combinations thereof, to achieve the required size scale for the particular sphincter. Sphincter assist device 1000 may be unitarily formed, or alternatively consist of a multi-piece assembly which may be snapped, interleaved, or bonded. It should be appreciated that material choice, manufacturing method, and assembly method effect the total force profile created by sphincter assist device 1000, and thus, may be chosen to tailor a desired non-linear force profile for a given sphincter.

Figure 5:
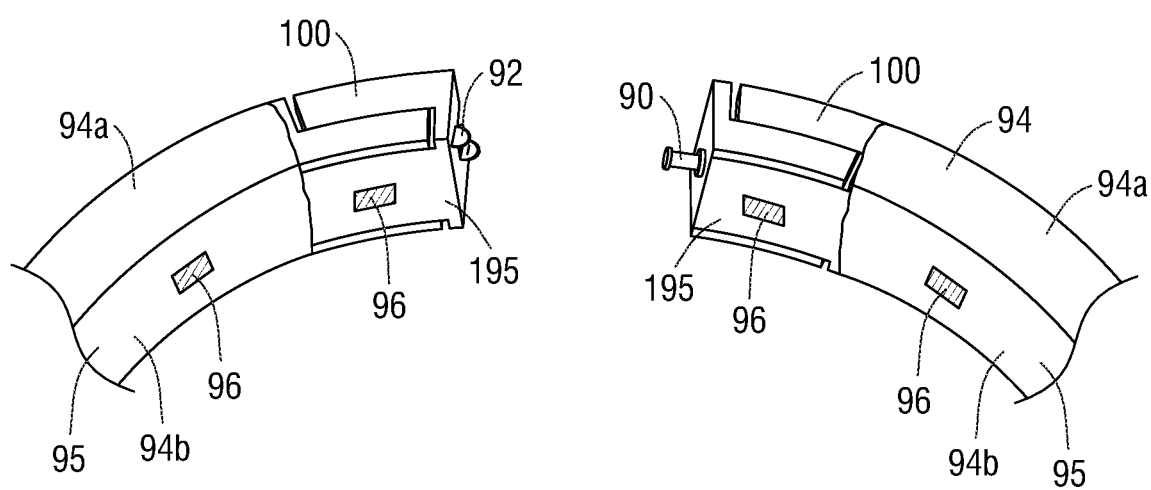
FIG. 5 is a side perspective partial view of the sphincter assist device of FIGS. 1A and 1B made up of a plurality of links of FIG. 3A including a connector and a protective sheath.

As illustrated in FIG. 5, a first link 100 may further include a male snap fit protrusion 90 and a second link 100 may include a female snap fit recess 92. Male snap fit protrusion 90 is configured to engage female snap fit recess 92 such that a first link 100 may engage a second link 100. Male snap fit protrusion 90 and female snap fit recess 92 facilitate implantation and placement of sphincter assist device 1000 about the sphincter. A plurality of links 100 coupled together may define separate segments of sphincter assist device 1000, which when coupled together via male snap fit protrusion 90 and female snap fit recess 92, form the ring which circumscribes the sphincter. In such an embodiment, the plurality of links 100 which form each segment of sphincter assist device 1000 may define a quarter circle, a half circle, a three-quarter circle, or any combination therebetween, such that when each respective segment of links 100 is coupled together a complete ring is formed which circumscribes the sphincter.

Figure 6:
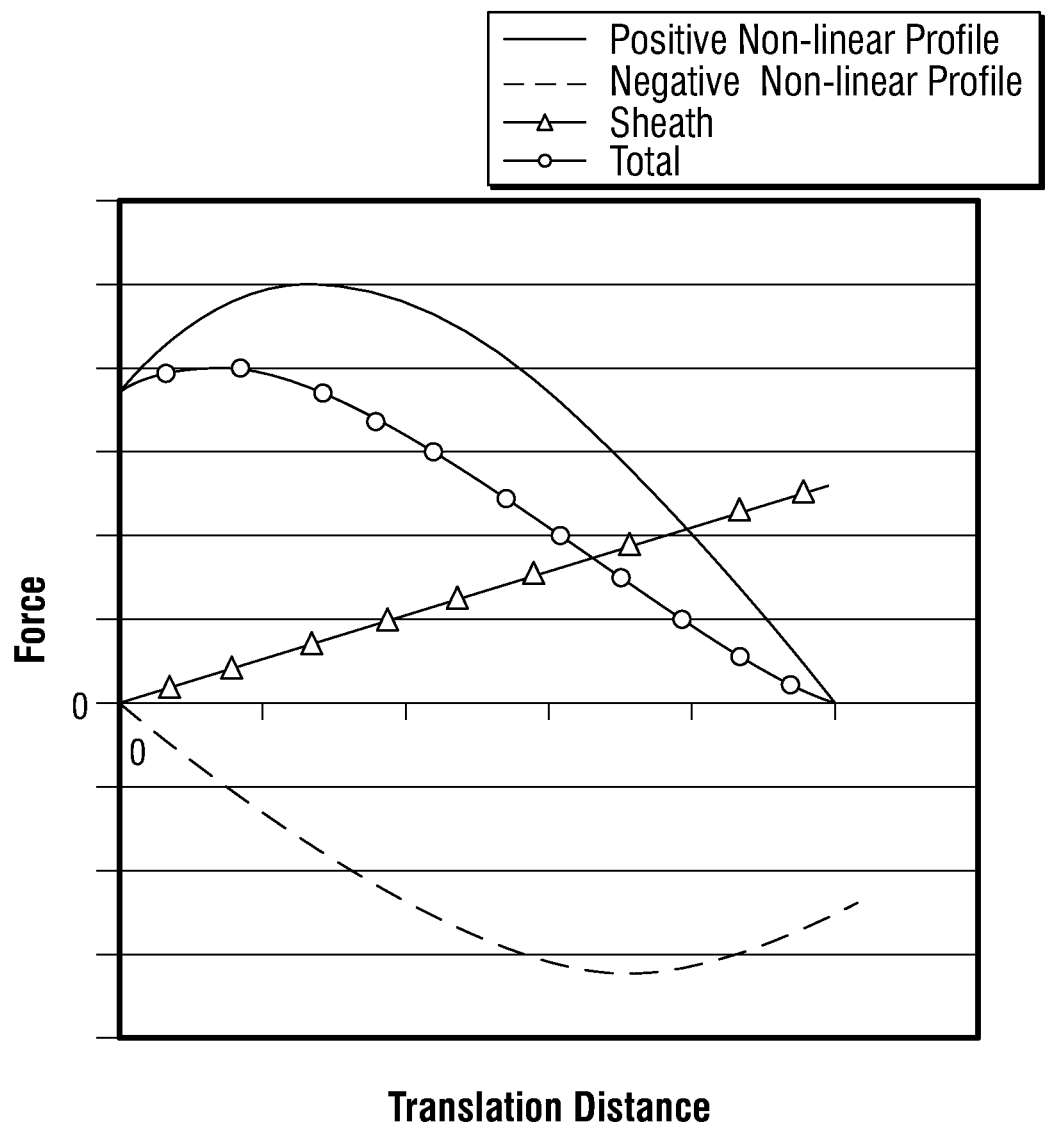
FIG. 6 is an exemplary graph of force versus translation distance of the sphincter assist device of FIGS. 1A and 1B made up of a plurality of links of FIG. 3A and a linear force profile of the protective sheath of FIG. 5.

As illustrated in FIG. 5, sphincter assist device 1000 may further include a protective sheath 94 which may enclose all of, or a portion of the plurality of links 100. Protective sheath 94 serves to prevent tissue ingrowth from affecting the performance of sphincter assist device 1000. Protective sheath 94 may be constructed from one or more biocompatible materials which may selectively prevent or promote tissue ingrowth as is known in the art, which may include elastic members, covers, or fillers. It is envisioned that protective sheath 94 may define a first material 94a to prevent tissue ingrowth, and a second material 94b which permits tissue ingrowth. In an embodiment, second material 94b may be radial in nature and disposed on a contact surface 95 of protective sheath 94 being oriented radially inward with respect to the sphincter, such that tissue ingrowth between the sphincter and contact surface 95 inhibits migration of protective sheath 94, and thus sphincter assist device 1000, away from the sphincter. It should be appreciated that an elastic member imparts a linear force profile similar to that of a rubber band device, as discussed above. FIG. 6 illustrates an exemplary graph of ($F_{magnitude}$) versus ($T_{distance}$) from the closed configuration to the open configuration wherein sphincter assist device 1000 includes protective sheath 94. As illustrated, protective sheath 94 adds a linear force profile which is incorporated into the total non-linear force profile of sphincter assist device 1000. Sphincter assist device 1000 may be tailored and configured such that the positive non-linear force profile and the negative non-linear force profile compensate for the linear force profile imparted by protective sheath 94, such that the total force profile of sphincter assist device 1000 maintains the non-linear force profile as discussed herein. Additionally, or alternatively protective sheath 94 may include pleats along a length thereof to allow easy expansion, where the pleats may be gathered by adhering a narrow strip of elastic material transverse to the length of the pleats. Further, protective sheath 94 may be pleated, or gathered in-between each respective link 100, where the gathered portions of protective sheath 94 facilitate and allow for expansion thereof.

Sphincter assist device 1000 may further include one or more tissue attachment points 96 disposed on a contact surface 195 of link 100, or contact surface 95 of protective sheath 94, such that tissue attachment and/or scarring is promoted therebetween to inhibit migration of sphincter assist device 1000 away from the implant location. In an embodiment, tissue attachment points 96 may define a feature, such as, for example, a loop, a slit, a cutaway, etc., such that a fastener, such as, for example, a suture, a tie, a clip, etc., may facilitate attachment of sphincter assist device 1000 and the sphincter. Migration away from the implantation decrease functionality of sphincter assist device 1000, or may render the functionality of sphincter assist device 1000 inoperable. It is envisioned that such tissue attachment points 96 are radial in nature, allowing the sphincter assist device 1000 to assume the open configuration to pass material through the sphincter passage.

Figure 7A:
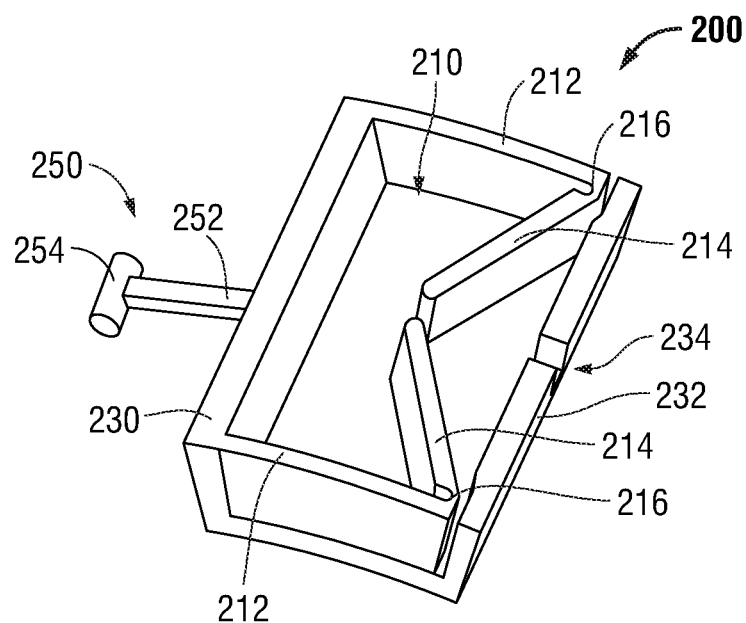
FIG. 7A is a side perspective view of another embodiment of a single link of the sphincter assist device of FIGS. 1A and 1B in accordance with the present disclosure.
Figure 7B:
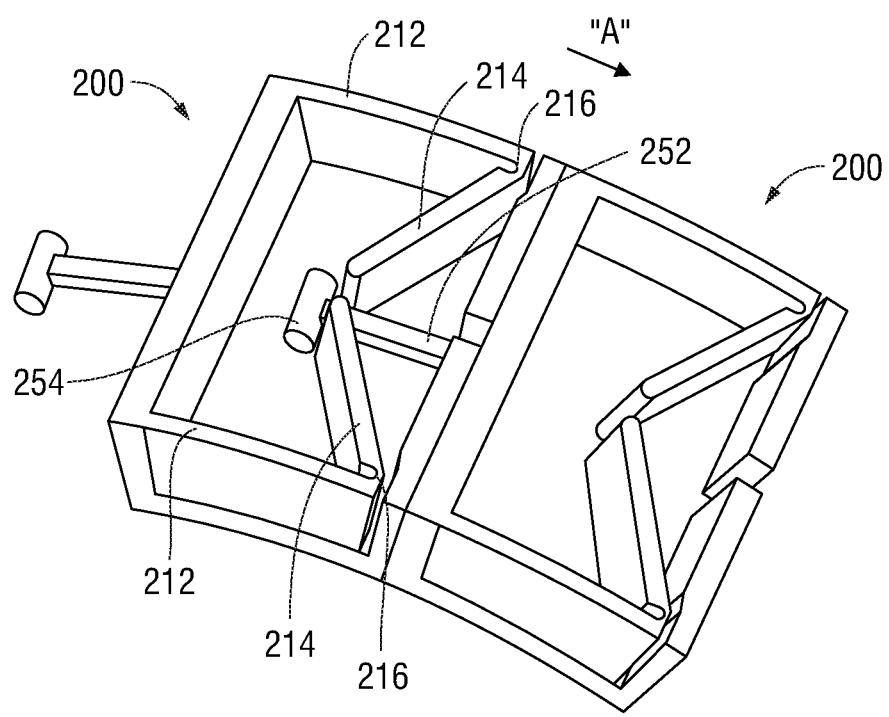
FIG. 7B is a side perspective view of a pair of links of FIG. 7A shown in the closed configuration.
Figure 7C:
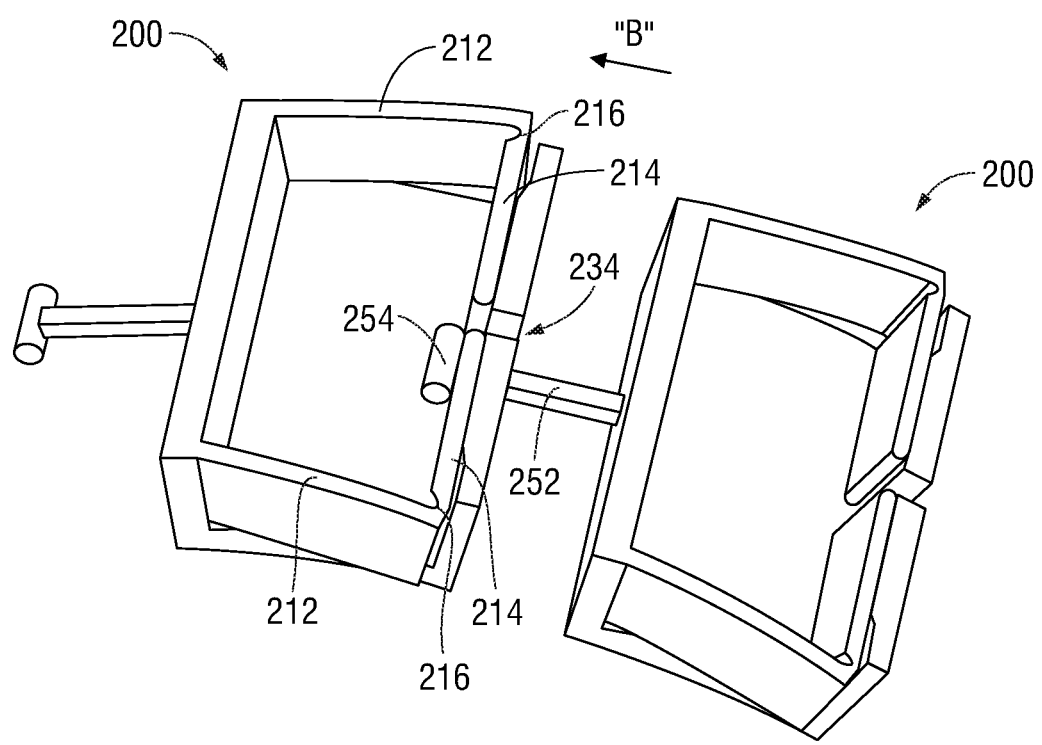
FIG. 7C is a side perspective view of a pair of links of FIG. 7A shown in the open configuration.

With reference to FIGS. 7A-7C, and in accordance with another embodiment of the present disclosures, a link 200 is illustrated which may make up sphincter assist device 1000. Link 200 includes similar features, aspects, and functionality to that of link 100 with respect to the non-linear force profile, and therefore, only distinctions and differences will be discussed herein. Link 200 maintains the non-linear force profile and creates a positive spring bias which biases sphincter assist device 1000 into the closed configuration. Link 200 includes a body section 210 and a latch cam 250 extending therefrom. The body section 210 includes a set of side beams 212 and a set of snap arms 214 coupled thereto. A hinge 216 is formed between each respective side beam 212 and snap arm 214. It should be appreciated that hinge 216 may include a living hinge to reduce components during manufacturing and assembly. Latch cam 250 includes a post 252 extending from a first wall 230 of body section 210 and a cam 254 disposed near an end of post 252. Body section 210 further defines a channel 234 along a second wall 232 configured to receive post 252 of an adjacent link 200 therethrough.

With reference to FIGS. 8A-8D, and in accordance with another embodiment of the present disclosure, a link 300 is illustrated which may make up sphincter assist device 1000. Link 300 also defines a non-linear force profile, where difference and distinctions of link 300 with respect to links 100 and 200 are described herein below. Similar to links 100 and 200, as link 300 translates away from an adjacent link 300 sphincter device 1000 is caused to radially expand and define a non-linear force profile, thus defining a larger inner diameter in the open configuration with respect to the closed configuration.

Figure 8A:
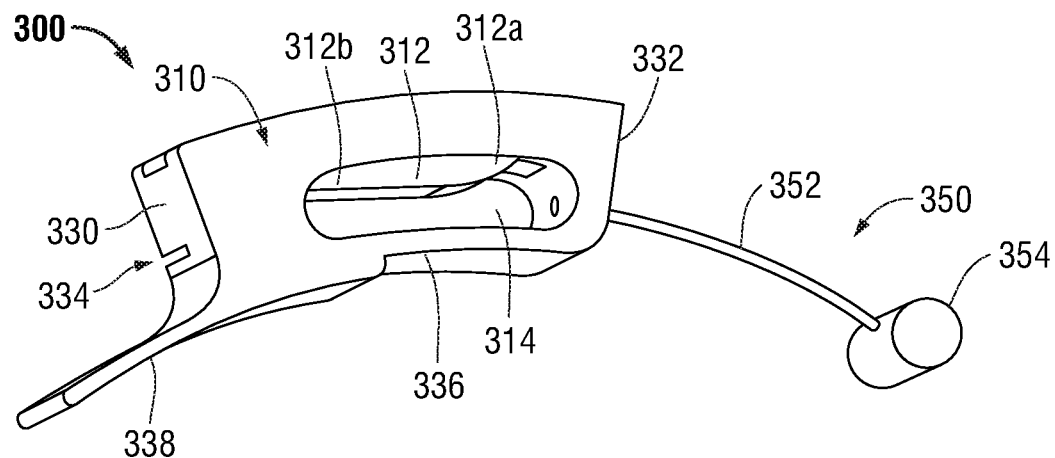
FIG. 8A is a side perspective view of an embodiment of a single latch of a sphincter assist device similar to the sphincter assist device of FIGS. 1A and 1B in accordance with the present disclosure.
Figure 8B:
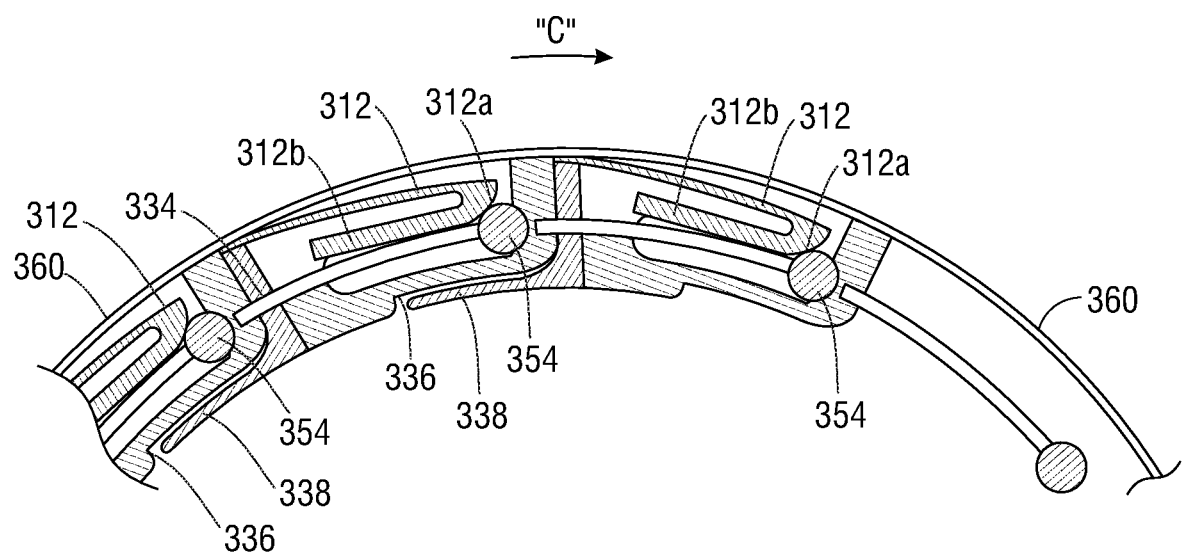
FIG. 8B is a cross-sectional view of a plurality of latches of FIG. 8A shown in the closed configuration.
Figure 8C:
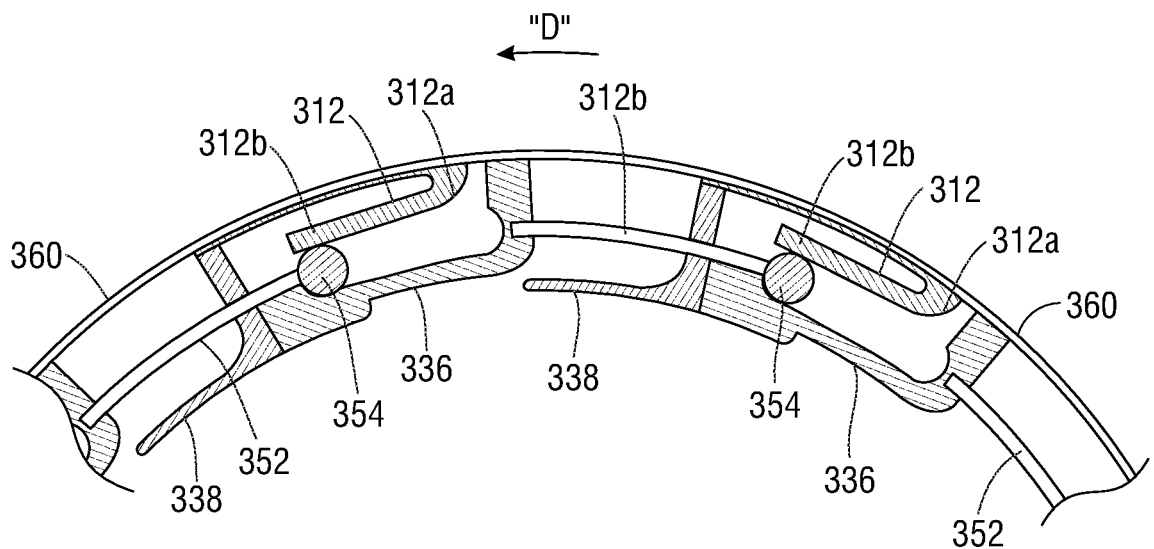
FIG. 8C is a cross-sectional view of a plurality of laches of FIG. 8A shown in the open configuration.
Figure 8D:
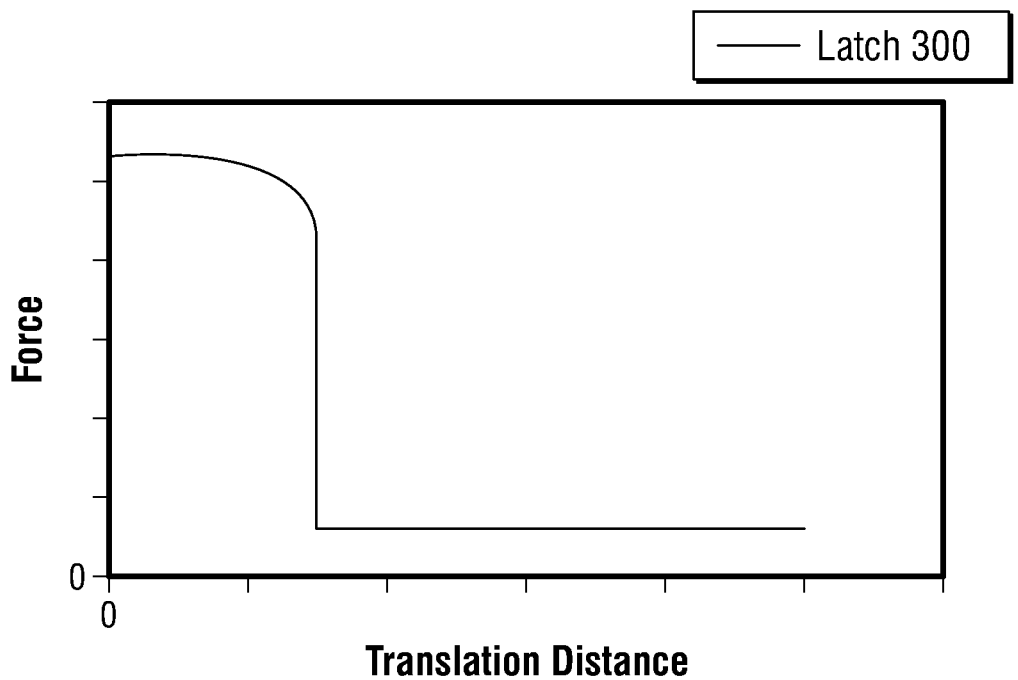
FIG. 8D is an exemplary graph of force versus translation distance of the sphincter assist device of FIGS. 1A and 1B made up of a plurality of latches of FIG. 8A.

Link 300 is configured such that a high magnitude of force ($F_{magnitude}$) is initially required as sphincter assist device 1000 begins to transition from the closed configuration towards the open configuration and a low, near constant restoring force is maintained once link 300 transitions into the open configuration. Thus, link 300 maintains an initial force requirement to translate sphincter assist device 1000 from the closed configuration towards to open configuration, while and also being configured to assist sphincter assist device 1000, and thus the sphincter, easily return from the open configuration to the closed configuration. More particularly, FIG. 8D illustrates an exemplary graph depicting ($F_{magnitude}$) versus ($T_{distance}$) from the closed configuration to the open configuration of link 300, wherein a high magnitude of force ($F_{magnitude}$) is required to begin the initial transition of sphincter assist device 1000 from the closed configuration towards the open configuration and a low, near constant magnitude of force ($F_{magnitude}$) is maintained in the open configuration. As discussed below, link 300 may be tailored to provide a desired initial magnitude of force in the closed configuration and a desired low, near constant magnitude of force in the open configuration such that link 300, and thus sphincter assist device 1000, may be tailored and configured for a given sphincter of a patient.

A plurality of interconnected links 300 may make up sphincter assist device 1000, where each link 300 is sequentially coupled to an adjacent link 300 to form a ring which circumscribes the sphincter. It should be appreciated that each link 300 which makes up sphincter assist device 1000 is generally identical, unless otherwise descried herein. Link 300 includes a body section 310 and a latch cam 350 extending therefrom. Body section 310 defines a spring mechanism 312 disposed within, and biased towards a cavity 314 of body section 310. Body section 310 further defines a channel 334 defined upon a first wall 330 of body section 310, wherein channel 334 is in communication with cavity 314. Body section 310 additionally includes a recess 336 disposed on an external surface thereof which extends from a second wall of 332. A finger 338 extends from first wall 330 and is configured to engage recess 336 of an adjacent link 300 (FIGS. 8B and 8C). Finger 338 is configured to be flexible and reduce tissue pinch points, blowouts, or tissue erosion by blocking or inhibiting tissue from entering into body section 310 when in the open configuration.

Latch cam 350 includes an arm 352 extending from second wall 330 of body section 310 and a cam 354 disposed near an end of arm 352. Arm 352 is configured to be received within channel 334 of an adjacent link 300, where cam 350 is configured to reside within cavity 314 and engage spring mechanism 312 of the adjacent link 300.

Spring mechanism 312 defines at least two separate force zones, a high force zone 312a and a low force zone 312b. It should be appreciated that the bias, curvature, and shape of spring mechanism 312 dictates the total force profile of link 300 as sphincter assist device 1000 transitions between the closed and open configurations. More particularly, spring mechanism 312 is configured to be biased into a position within cavity 314. As a first link 300 translates away from an adjacent link 300 in the direction of arrow "C" (FIG. 8B), i.e., as sphincter assist device 1000 transitions from the closed configuration towards the open configuration, arm 352 translates within channel 334 of the adjacent link 300 and cam 354 rides along spring mechanism 312 of the adjacent link 300. As cam 354 rides along and imparts a force upon the contour of the high and low force zones 312a and 312b of spring mechanism 312, whereby the bias of spring mechanism 312 imparts resistance force thereon, the non-linear force profile of link 300, and thus sphincter device 1000, is created. As depicted herein, a ramped portion defines the high force zone 312a and a near flat portion defines the low force zone 312b. It is further envisioned that spring mechanism 312 may define a plurality of high force zones 312a or low force zones 312b, and/or define an angled surface of varying degrees to adjust the high force zone 312a or low force zone 312b, to further tailor and configure the non-linear force profile of link 300, and thus sphincter device 1000, for a given sphincter of a patient.

Link 300 may further include an elastic band 360 which circumscribes the plurality of links 300 making up sphincter assist device 1000. Elastic band 360 is configured to provide a low spring force radially inward to facilitate closure of sphincter assist device 1000. By varying the elasticity of elastic band 360, in combination with the bias and configuration of spring mechanism 312, sphincter assist device 1000 may be further tailored and configured for a given sphincter of a patient.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A sphincter assist device, comprising:
    a plurality of interconnected links defining a ring, each link including:
        a body section defining a cavity and a channel extending from a first wall of the body section to the cavity;
        a finger extending from the first wall;
        a spring mechanism disposed within the cavity of the body section; and
        a latch cam extending from a second wall of the body section and engageable with the spring mechanism of an adjacent link of the plurality of links, wherein the spring mechanism of the adjacent link exerts a positive non-linear force on the latch cam thereby defining a non-linear force profile during transition of the sphincter assist device between open and closed configurations.

2. The sphincter assist device of claim 1, wherein the latch cam is configured to extend through the channel of the adjacent link of the plurality of links and into the cavity of the adjacent link of the plurality of links.

3. The sphincter assist device of claim 1, wherein the latch cam includes an arm extending from the second wall of the body section and a cam member disposed at a distal portion of the arm.

4. The sphincter assist device of claim 3, wherein the arm of the latch cam is configured to extend through the channel of the adjacent link of the plurality of links and the cam member is configured to slide along the spring mechanism of the adjacent link of the plurality of links.

5. The sphincter assist device of claim 1, further comprising a protective sheath enclosing the plurality of links.

6. The sphincter assist device of claim 1, further comprising a recess defined along a portion of an external surface of the body section.

7. The sphincter assist device of claim 6, wherein the finger is configured to engage the recess of another adjacent link of the plurality of links.

8. The sphincter assist device of claim 6, wherein the finger is flexible and is configured to inhibit tissue from entering the cavity of the body section.

9. The sphincter assist device of claim 1, wherein the spring mechanism defines at least two separate force zones.

10. The sphincter assist device of claim 1, further comprising an elastic band circumscribing the plurality of links and configured to provide a spring force radially inward to facilitate movement of the sphincter assist device from the open configuration to the closed configuration.

11. A link for use in a sphincter assist device, the link comprising:
    a body section defining a cavity and a channel, the channel extending from a first wall of the body section to the cavity;
    a finger extending from the first wall;
    a spring mechanism disposed within the cavity of the body section; and
    a latch cam extending from a second wall of the body section and engageable with a spring mechanism of a first adjacent link, wherein the spring mechanism of the link is configured to exert a positive non-linear force on a latch cam of a second adjacent link thereby defining a non-linear force profile during transition of the sphincter assist device between open and closed configurations.

12. The link of claim 11, wherein the latch cam is configured to extend through a channel of the first adjacent link and into a cavity of the first adjacent link.

13. The link of claim 11, wherein the latch cam includes an arm extending from the second wall of the body section and a cam member disposed at a distal portion of the arm.

14. The link of claim 13, wherein the arm of the latch cam is configured to extend through a channel of the first adjacent link and the cam member is configured to slide along the spring mechanism of the first adjacent link.

15. The link of claim 11, wherein the finger is configured to engage a recess of the second adjacent link.

16. The link of claim 11, wherein the finger is flexible and is configured to inhibit tissue from entering into the cavity of the body section.

17. The link of claim 11, further comprising a recess defined along a portion of an external surface of the body section.

18. The link of claim 11, wherein the spring mechanism defines at least two separate force zones.

* * * * *